United States Patent [19]

Peterson

[11] Patent Number: 4,792,689

[45] Date of Patent: Dec. 20, 1988

[54] METHOD FOR OBTAINING A RATIO MEASUREMENT FOR CORRECTING COMMON PATH VARIATIONS IN INTENSITY IN FIBER OPTIC SENSORS

[75] Inventor: John I. Peterson, Falls Church, Va.

[73] Assignee: The United States of America as represented by the Department of Health and Human Services, Washington, D.C.

[21] Appl. No.: 129,387

[22] Filed: Nov. 24, 1987

Related U.S. Application Data

[63] Continuation of Ser. No. 796,782, Nov. 12, 1985, abandoned.

[51] Int. Cl.⁴ ............................................. G01N 21/64
[52] U.S. Cl. .............................. 250/458.1; 250/227; 356/417
[58] Field of Search ............... 356/317, 318, 417, 445; 250/227, 458.1, 459.1, 461.1, 461.2; 422/57, 68; 436/172

[56] References Cited

U.S. PATENT DOCUMENTS 4,061,578 12/1977 Kleinerman ................. 250/461.1 X
4,558,217 12/1985 Aluas ................................. 250/227

Primary Examiner—F. L. Evans
Attorney, Agent, or Firm—Browdy and Neimark

[57] ABSTRACT

A method for correcting common path variations in intensity in fiber optic chemical sensing devices uses a device for spatially separating light of different wavelength regions and a dye system selected so that light passing back to a measuring system along the fiber optic sensor consists of two wavelength regions. The first wavelength region varies with the concentration of analyte, and the other wavelength region is insensitive to the concentration of analyte.

8 Claims, 1 Drawing Sheet

METHOD FOR OBTAINING A RATIO MEASUREMENT FOR CORRECTING COMMON PATH VARIATIONS IN INTENSITY IN FIBER OPTIC SENSORS

This application is a continuation, of application Ser. No. 796,782, filed Nov. 12, 1985, now abandoned.

BACKGROUND OF THE INVENTION

The present invention relates to a method for correcting variations in intensity in fiber optic chemical sensors based on wavelength discrimination of indicator dye combinations.

Various measuring devices are known for measuring a physical parameter by measuring the intensity of a light beam. Such measuring devices are used for measuring parameters such as pressure, temperature, and flow rate. These fiber optic measuring devices usually include a fiber optical transmission line or cable, a light source illuminating the first end of the transmission line, a sensor or transducer arranged on the second end of the transmission line for measuring the physical parameter by means of the transmitted light and for returning a corresponding light intensity into the second end of the line, a branching element or coupler on the first end side, a photodetector for measuring the returned light, and a signal processing device connected to the photodetector for issuing an output signal in accordance with the parameter.

The sensor on the measurement side of such a measuring device may contain a reflector which is movable in dependence on the physical parameter either perpendicularly or parallel to the end face of the fiber optical transmission line.

In such measuring devices, th fiber optical transmission line is exposed to the influence of the environment, for example, to temperature changes, mechanical stress, irradiation, vibrations, etc. These effects or influences caused by the effects may create light losses in the fiber optic transmission line. These and other effects, for example, bending of the fibers, may introduce errors in the measurements and therefore may result in erroneous readings. For this reason, means are required to compensate for such errors.

Fiber optic chemical sensors involve the absorption or emission of light by an analyte sensitive reagent at the end of a fiber optic lead. The intensity of light transmitted through or emitted by the reagent is a function of the analyte concentration in a certain wavelength region of the light. Typical examples of this are an absorptiometric color indicator for pH measurement, such as phenol red, where green light is absorbed by the dye as a function of increasing pH, so that the transmittance of green light through the dye indicator decreases with pH. Another such example is a fluorescent indicator dye, such as that used for oxygen measurement, where the dye is excited to fluorescence by blue or ultraviolet light and the fluorescent green light which is emitted varies in intensity with oxygen pressure. Other types of fiber optic sensors are similar, with the intensity of the light returning along the fiber to the measuring instrument from the sensing end aarying with the analyte concentration. It is desirable to have some method of correcting for variations in the intensity of light in the fiber optic system which are not analyte dependent, particularly those variations which result from fiber bending, and for variations in the illumination source.

With a fiber optic sensor which consists of two optical fibers joined at or before the sensor end, with one fiber collecting light from the illumination system and the other fiber returning light to the measurement system, such compensation has been relatively simple, as shown in FIG. 1. In the case of an absorptiometric indicator, the illuminating light can consist of two wavelength regions which pass through the dye indicator and back along the other fiber to the measurement system. Both wavelength regions have a common optical path. Light of one wavelength region is absorbed by the indicator as a function of analyte concentration, and the other wavelength region is not absorbed by the indicator. As a result, the ratio of the intensities of these two wavelength regions provides a measure of analyte concentration, and other optical variations (common path variations) cancel out. In the case of a fluorescent indicator, the same system has been used, with the excitation wavelength region of light returning to the measurement system along with the analyte sensitive fluorescent light in a different wavelength region, and the ratio of the intensities of the two wavelength regions compensates for common path variations. Existing fiber optic chemical sensors are based on this (cf. Peterson et al., *Analytical Chemistry* 52, 864 (1980); and ibid 56, 62 (1984); and U.S. Pat. 4,200,110.

Single fiber chemical sensors can also be made. Here, a single fiber with analyte sensitive reagent at one end is connected at its other end to the measuring instrument. An optical system in the instrument injects light into the end of the single fiber and observes light coming out of the same fiber for measurement. There are fuur general methods of combining and separating the entrance and exit beams in a single fiber chemical sensor.

The first is to use a bifurcated fiber or coupler which joins two fibers into one. This is equivalent to the dual fiber system.

The second is to use a partially reflecting mirror arranged so that the illumination light is reflected into the end of the single fiber, some being lost by passage through the mirror, as shown in FIG. 2. Light returning from the fiber passes through the mirror to a measuring system, with some light being lost by reflection. This achieves the same result as a dual fiber system but is not attractive because of the large light loss at the partially reflecting mirror.

The third method is to use a spatial filter, which makes use of the fact that light can be launched into a fiber in a collimated beam of diameter similar to the fiber diameter, and light exits from the fiber in a conical path so that it can be collected by a lens or reflector of large diameter, losing only the light which exits along the small diameter entrance path, as shown in FIG. 3. With this arrangement, the same compensating methods described for the dual fiber sensor can be used, although stray light problems make an alternative system attractive.

Ruell et al., in U.S. Pat. No. 4,356,396, disclose a fiber optical measuring device which compensates for losses in optical joints by passing a first wavelength through a mirror in front of a sensor and a second wavelength through the sensor and to a mirror behind the sensor. Both wavelengths are then reflected back to a detector and a ratio of intensities of the signals is obtained.

Another fiber optic system for measuring chemical and/or physical quantities is shown in Brogardh et el., U.S. Pat. No. 4,446,366. The device used has a monitoring transducer with a response spectrum which within the emission spectrum of the incident light source gives rise to an emitted light spectrum of the incident light on he quantity to be measured, which emitted light spectrum emanates from the measuring transducer, and at least one wavelength interval of the emission spectrum of the incident light source has a dependence on the quantity to be measured. Tne quantity to be measured is not identical to the corresponding dependence in at least one other non-identical wavelength interval of the emission spectrum of the incident light source. The optical fiber means has filtering spectra which divide the emitted spectrum, emanating from the transducer into at least three non-identical wavelength intervals, which can overlap, and a photo detector which is arranged to measure the emitted light after filtering and generate detector signals in the respective wavelength interval. The measuring transducer consists of a material with an optical absorption edge which, within one wavelength interval, coincides with the emission spectrum, and the dependence of the response spectrum of the measuring transducer on the quantity to be measured involves wavelength displacement and/or deformation of the absorption edge. Alternatively, the measuring transducer may consist of at least one filter of interference type having transmission or reflection spectra which vary with the quantity to be measured within the emission spectrum. None of the prior art shows the use of light emitted at two wavelengths, one which results in fluorescence which is analyte sensitive and the other which results in fluorescence which is analyte non-sensitive.

SUMMARY OF THE INVENTION

The present invention is directed to a method of correcting for common path variation in intensity in fiber optic sensors. Two wavelengths of light are passed through a single sample. One wavelength results in the fluorescent emission from the sample of light which is analyte sensitive. The other wavelength results in the emission of light from the sample which is analyte non-sensitive. In order to accomplish both analyte sensitive and analyte non-sensitive fluorescent emission, two fluorescent indicators are used. One fluorescent indicator is analyte sensitive, and the other fluorescent indicator is analyte non-sensitive.

The method of the present invention (the fourth general method of making a single fiber chemical sensor) involves the use of dichroic filters or mirrors, which reflect light in one wavelength region and transmit light in another wavelength region. Other devices which spatially separate light of different wavelength regions can be used in addition to or instead of the dichroic mirror. A typical arrangement, with appropriate light channeling optics, is with the illumination light of one wavelength being reflected into the optical fiber by a dichroic mirror for excitation of sensor fluorescence. The light returning from the sensor consists of both the illumination light scattered back and the fluorescent emitted light. The light of the illuminatio wavelength follows the same optical path from where it came, back to the lamp which was the source thereof. The fluorescent light, of different wavelength, passes through the dichroic filter to a measurement system. In order to achieve a common path correction, it is necessary for the returning fluorescent light to consist of two wavelength regions, one analyte sensitive and one not analyte sensitive. Since both wavelength regions follow the same optical path back from the sensor through the optical fiber and through the dichroic filter, a separation of the wavelength regions and measurement of the ratio of their intensities provides a signal corrected for variations common to both. The present invention is directed to the use of two wavelength regions of light emitted by a sensor and returning to the measurement system along the optical fiber, one region being analyte sensitive and the other region not analyte sensitive, so that the ratio of their intensities gives a signal corrected for intensity variations along the common optical path. This also provides a correction for variations in illumination intensity, since the light emitted at the sensor varies in intensity in proportion to variations in intensity of the illumination light exciting the fluorescence or phosphorescence of the indicator.

It is theoretically possible to use a fluorescent indicator which has one fluorescent wavelength region which is analyte sensitive and another region which is not analyte sensitive, so that the ratio of these two regions can be measured. This is, in practice, difficult to achieve, and it is more practical to use mixtures of dyes of luminescent materials. A requirement is that one of the dyes of the mixture should have a large Stokes shift, i.e., a relatively long gap between the excitation wavelength region and the emission wavelength region, so that the emitting region of the other dye can fit between, as shown in FIG. 5. The reason for this is that if one dye absorbs in a wavelength region where the other emits, they will not emit light independently. One example is a pair of dyes, both of which absorb light in the blue region, and one of them emits geeen light and one of them emits red light. The green emitter is analyte sensitive and the red one is not. All of the light from the sensor passes back along the fiber. The blue illumination light is reflected back to the lamp by the first dichroic filter, and the green and red light pass through and are split, one passing through and one being reflected by a second dichroic filter so that their intensities can be measured separately and the ratio taken by appropriate measuring means.

A similar system can be used for an optical absorption indicator dye where, for example, a fluorescent dye or luminous material is combined with the absorption indicator dye. The excitation light causes the fluorescent dye to emit light which is absorbed in one wavelength region by the indicator dye as a function of analyte concentration, and to emit light in another wavelength region which is transmiteed through the indicator dye without variation of its intensity by the analyte. It is necessary that the indicator dye not absorb light in the same wavelength region as the luminescent dye is excited, otherwise the luminescence will not occur or will be analyte dependent.

DESCRIPTION OF THE DRAWINGS

FIG. 1 shows a prior art fiber optic sensor consisting of two optical fibers, 12 and 13, joined at or before the sensor end, with one fiber 11 collecting light from the illumination system and the other fiber, 10, returning light from the dye indicator 14 to a measurement system.

FIG. 2 shows a prior art single fiber sensor wherein a partially reflecting mirror 22 is arranged so that illumination light 21 is reflected in the end of the single fiber 20. Light returning from the dye indicator 24 through the fiber passes through the mirror to a measuring system 23.

FIG. 3 shows a prior art single fiber spatial filtering method. The spatial filter makes use of the fact that light can be launched into a fiber 30 in a collimated beam 31 of diameter similar to the fiber diameter, and light exits from the fiber in a conical path so that it can be collected by a lens or reflector of large diameter 33.

FIG. 4 shows an example of a single fiber, wavelength separation arrangement wherein dichroic mirrors, 41 and 46 are used for wavelength separation. The single optical fiber 40 is illuminated with illumination light 44 which contacts the dye indicator 42 (sensor). The dichroic mirror, 41, separates the wavelength into analyte sensitive wavelength, 43, and not analyte sensitive wavelength, 45. Illumination light of one wavelength is reflected into the optical fiber by a dichroic mirror or other device for excitation of sensor fluorescence. The light returning from the sensor consists of both the illumination light scattered back and the fluorescent emitted light. The light of the illumination wavelength follows the same optical path from whence it came, back to the lamp 58. The fluorescent light, of different wavelength, passes through the dichroic filter 46 to a measurement system 60, including mirror 41. Other dichroic mirror arrangements can be used in an equivalent way, or other wavelength separating devices.

FIG. 5 shows the desired gap between emission wavelength region and excitation wavelength region so that the emitting region of another dye can fit in. The curve 50 shows the excitation of both dyes in the emitting region. The curve 51 shows the wavelength of one dye in the emission region. Curve 52 shows the wavelength of another dye in the pair in the emission region. The emitting region of one dye, shown at 51, fits between the excitation wavelength region and the emission wavelength region of the other dye, shown at 51.

Figure 1:
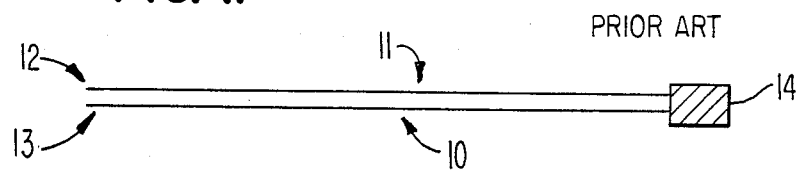
FIG. 1 shows a dual fiber system for chemical analysis.
Figure 2:
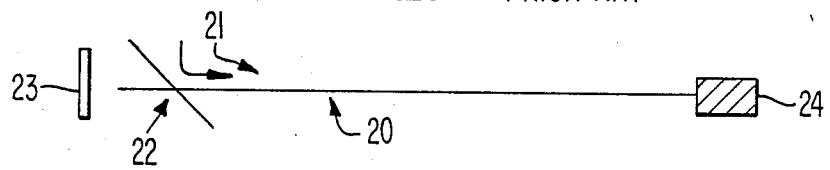
FIG. 2 shows a single fiber, partial mirror system for analysis.
Figure 3:
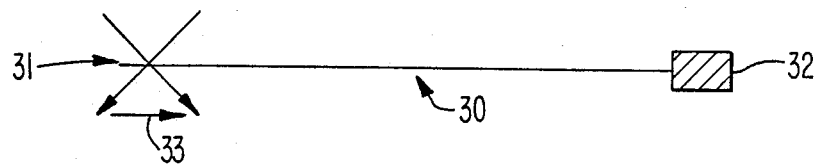
FIG. 3 shows a single fiber, spatial filtering method for analysis.
Figure 4:
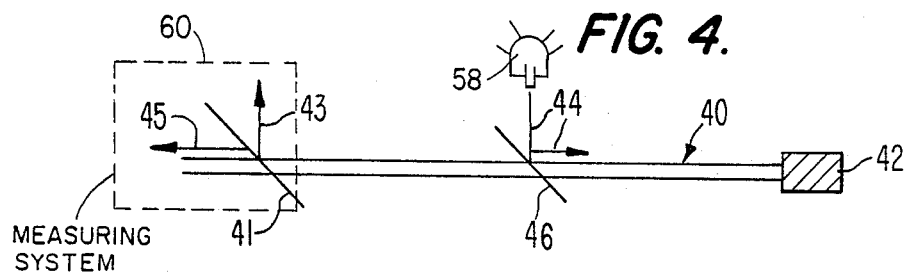
FIG. 4 shows a single fiber, wavelength region separation method of analysis.
Figure 5:
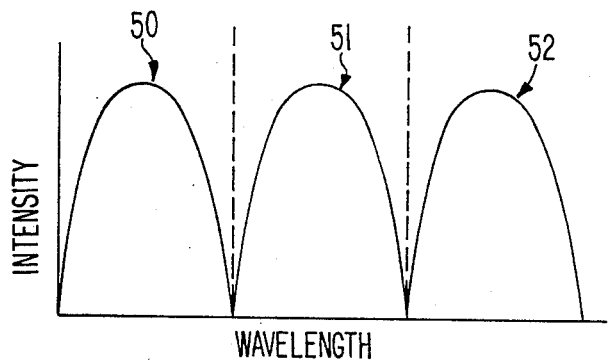
FIG. 5 illustrates suitable wavelength variables for use in choosing paired dyes.

The invention requires the use of combinations of dyes and luminescent materials in a fiber optic chemical sensor with the proper characteristics of absorption and emission of light, so that the light passing back to the measuring system 60 along the fiber will consist of two wavelength regions, other than the wavelength of the illumination light. These two wavelength regions consist of one wavelength region whose intensity varies as a function of analyte concentration in the indicator 41, so that a measurement of the ratio of these intensities, as obtained by the measuring system, is a measure of the analyte concentration corrected for variations in the system which may affect the intensity, other than the analyte.

It will be obvious to those skilled in the art that various changes may be made without departing from the scope of the invention and the invention is not to be considered limited to what is shown in the drawings and described in the specification.

What is claimed is:

1. A fiber optic sensing system for measuring the concentration of an analyte, said system comprising:
   an otpical fiber having a first end and a second end;
   a light source for illuminating said optical fiber, at said first end or between said first and second ends, with illumination light of a first wavelength region directed toward said second end of said optical fiber;
   a sensor optically connected to said second end of said optical fiber, said sensor including a mixture of a first and a second indicator dye, said first indicator dye, when illuminated by said light of said first wavelength region, emitting light of a second wavelength region at an intensity sensitive to the concentration of the analyte to be measured, said second indicator dye, when illuminated by said light of said first wavelength region, emitting light of a third wavelength region at an intensity insensitive to the concentration of the analyte to be measured, said first, second and third wavelength regions differing from each other and being essentially non-overlapping;
   means for spatially separating light of said first wavelength region reflected by said sensor into second end of said optical fiber from said light of said second and third wavelength regions emitted by said indicator dyes;
   means for measuring the ratio of the intensities of said second and third wavelength regions with respect to each other, thereby producing a corrected signal corresponding to the concentration of hhe analyte to be measured, said measuring means including means for spatially separating light of said second and third wavelength regions from each other.

2. The device of claim 1, wherein the means for spatially separating light of said second and third wavelength regions from each other is a dichroic mirror.

3. A method for correcting common path variations in intensity in fiber optic chemical sensing devices, comprising the steps of:
   admitting an analyte into a sensor of an optical fiber having a first end an a second end;
   illuminating said optical fiber, at said first end or between said first and second ends, with illumination light of a first wavelength region directed toward a second end of said optical fiber, said sensor being optically connected to said second end of said optical fiber, said sensor including a mixture of a first and a second indicator dye, said first indicator dye, when illuminated by said light of said first wavelength region, emitting light of a second wavelength region at nn intensity sensitive to the concentration of said analyte, said second indicator dye, when illuminated by said light of said first wavelength region at an intensity sensitive to the length region at an intensity insensitive to the concentration of said analyte, said first, second and third wavelength regions differing from each other and being essentially non-overlapping;
   spatially separating light of said first wavelength region reflected by said sensor from light of said second and third wavelength regions emitted by said indicator dyes;
   spatially separating light of said second and third wavelength regions from each other;
   measuring the ratio of the intensities of said second and third wavelength regions with respect to each other, thereby producing a corrected signal corresponding to the concentration of the analyte to be measured.

4. The method of claim 3, wherein the indicator dye mixture includes a dye selected from the group consisting of fluorescent dyes and phosphorescent dyes.

5. The method of claim 4, wherein the indicator dyes are fluorescent.

6. The method of claim 4, wherein the indicator dyes are phosphorescent.

7. The method of claim 3, wherein the indicator dye mixture comprises a pair of dyes which both absorb in the blue region, one dye emits green light and the other dye emits red light.

8. The method of claim 3, wherein dichronic mirror means are used for spatially separating light of different wavelength regions from each other.

* * * * *